(12) United States Patent
Nobutoki et al.

(10) Patent No.: US 6,704,663 B2
(45) Date of Patent: Mar. 9, 2004

(54) METHOD OF CALCULATING MAGNETIC INTERACTION OF MOLECULES USING LOCALIZED MAGNETIC ORBITAL

(75) Inventors: Hideharu Nobutoki, Tokyo (JP); Suguru Nagae, Tokyo (JP)

(73) Assignee: Mitsubishi Denki Kabushiki Kaisha, Tokyo (JP)

( * ) Notice: Subject to any disclaimer, the term of this patent is extended or adjusted under 35 U.S.C. 154(b) by 0 days.

(21) Appl. No.: 10/279,913

(22) Filed: Oct. 25, 2002

(65) Prior Publication Data

US 2003/0204324 A1 Oct. 30, 2003

(30) Foreign Application Priority Data

Apr. 26, 2002 (JP) ........................... 2002-126291

(51) Int. Cl.[7] .............................................. G06F 19/00
(52) U.S. Cl. ........................................................ 702/27
(58) Field of Search .............................. 702/27; 600/9; 422/186; 250/423; 424/1.65, 9.361; 360/324; 435/69, 288; 204/1.57

(56) References Cited

U.S. PATENT DOCUMENTS 4,105,921 A * 8/1978 Bartlett et al. ........... 250/423 P
5,688,486 A * 11/1997 Watson et al. ............. 424/1.65
2002/0106314 A1 * 8/2002 Pelrine et al. .............. 422/186
2003/0028070 A1 * 2/2003 Jacobson ...................... 600/9

FOREIGN PATENT DOCUMENTS

JP 11-006825 1/1999

OTHER PUBLICATIONS

Sakama, Akimasa; "Theoretical Study on the Exchange Constants of the Transition Metals", Hitachi Metals Technical Journal, 16(2000).

* cited by examiner

Primary Examiner—John Barlow
Assistant Examiner—Tung Lau
(74) Attorney, Agent, or Firm—Leydig, Voit & Mayer, Ltd.

(57) ABSTRACT

A magnetic interaction is calculated by expressing a localized magnetic orbital as a linear combination of molecular orbitals and determining a localized magnetic orbital to be calculated from a maximum overlap condition evaluated between a reference orbital localized in anatomic orbital and the localized magnetic orbital. Another magnetic interaction is calculated by expressing a localized magnetic crystal orbital as a linear combination of crystal orbitals and determining a localized magnetic crystal orbital to be calculated from the maximum overlap condition.

6 Claims, 4 Drawing Sheets

METHOD OF CALCULATING MAGNETIC INTERACTION OF MOLECULES USING LOCALIZED MAGNETIC ORBITAL

BACKGROUND OF THE INVENTION

1) Field of the Invention

The present invention relates to a technology for calculating magnetic interaction of molecules, crystalline compounds, and high polymer compounds exhibiting ferromagnetism.

2) Description of the Related Art

Conventionally, a theory of magnetic characteristics has developed using a Heisenberg model which targets a localized electron system and a Stoner model which targets an itinerant electron system. However, since the Heisenberg model produces a rough approximation and cannot be easily handled, the Heisenberg model has been culled out in favor of the Stoner model.

The Stoner model has passed through a physical examination in a Hubbard model, an Anderson model, or the like which are phenomenological models and, at present, has settled to a band calculation method based on a density functional theory. In the recent band calculation method based on the density functional theory, an effective exchange interaction energy can be obtained with a calculation accuracy which is satisfactory to some extent (Sakuma Akimasa, Hitachi Metals Technical Journal, 16, 55 to 60 (2000)).

However, the conventional evaluation method (band calculation method) targets, for calculation, an itinerant electron system which uses a Bloch function as a base, and, therefore, it has been difficult to handle a localized electron system or an intermediate electron system between the itinerant electron system and the localized electron system.

The band calculation method can be easily applied to an extremely small crystal system such as iron or nickel crystals and oxides thereof. However, even though the band calculation method is applied to a small crystal system, an enormous quantity of calculation is required. Therefore, the following problem is left. That is, for example, it is substantially difficult to apply the band calculation method to an actual huge crystal system such as a neodymium-based rare earth magnetic material ($Nd_2Fe_{14}B$ crystal) from the viewpoint of calculation quantity.

On the other hand, in consideration of the circumstances, a method of easily predicting ferromagnetism by changing molecular orbitals has been proposed (Japanese Patent Application Laid-Open No. H11-6825). However, magnetic characteristics detected in an experiment cannot be calculated using this method, and the calculation is limited to an organic high polymer compound. For this reason, the method poses a problem in a practical use.

SUMMARY OF THE INVENTION

It is an object of this invention to obtain a method of calculating a magnetic interaction in not only an itinerant electron system but also a localized electron system or an intermediate electron system across both the electron systems.

The magnetic interaction calculation method according to one aspect of this invention comprises calculating a magnetic interaction of molecules using a localized magnetic orbital $\eta_a$ which satisfies a maximum overlap condition $$\sum_a |\langle \eta_a | \omega_a \rangle| = \text{maximum, wherein}$$

$$\eta_a = \sum_i T_{ai} \phi_i$$

and $\omega_a$ is a reference orbital given by $$\omega_a = \sum_i c_{ai}^{-1} \phi_i$$

where $$\phi_i = \sum_a c_{ai} \chi_a$$

is a molecular orbital expressed as a linear combination of an atomic orbital $\chi_a$, $c_{ai}$ is an expansion coefficient, $c_{ai}^{-1}$ is an inverse matrix of the expansion coefficient $c_{ai}$, and $T_{ai}$ is the expansion coefficient of the a-th orbital $\eta_a$ for the i-th molecular orbital $\phi_i$.

The magnetic interaction calculation method according to another aspect of this invention comprises calculating a magnetic interaction of crystalline compounds or high polymer compounds using a localized magnetic crystal orbital $\eta_a$ (k) which satisfies a maximum overlap condition $$\sum_a |\langle \eta_a | \omega_a \rangle| = \text{maximum, wherein}$$

$$\eta_a(k) = \sum_i T_{ai}(k) \phi_i(k)$$

and $\omega_a$ (k) is a reference orbital given by $$\omega_a(k) = \sum_i c_{ai}(k)^{-1} \phi_i(k)$$

where $$\phi_i(k) = \sum_a c_{ai}(k) \sum_R \exp(ikR) \chi_a(R)$$

is a crystal orbital expressed as a linear combination of an atomic orbital $\chi_a$, $c_{ai}$ (k) is an expansion coefficient, $c_{ai}$ (k)$^{-1}$ is an inverse matrix of the expansion coefficient $c_{ai}$ (k), $T_{ai}$ (k) is the expansion coefficient of the a-th localized magnetic orbital $\eta_a$ (k) for the i-th crystal orbital $\phi_i$ (k), k is a wave vector ranging from $-\pi/c$ to $\pi/c$ where c is primitive vectors, and R is a vector representing crystal periods.

The magnetic characteristic value calculation method according to still another aspect of this invention comprises calculating a magnetic characteristic value based on each of the magnetic interaction calculation methods.

The program according to still another aspect of this invention causes, when executed on a computer, the computer to execute each of the magnetic interaction calculation methods.

The program according to still another aspect of this invention causes, when executed on a computer, the computer to execute each of the magnetic characteristic value calculation methods. Each of the magnetic characteristic value calculation methods comprises calculating a magnetic characteristic value based on each of the magnetic interaction calculation methods.

These and other objects, features and advantages of the present invention are specifically set forth in or will become apparent from the following detailed descriptions of the invention when read in conjunction with the accompanying drawings.

DETAILED DESCRIPTION

Figure 1:
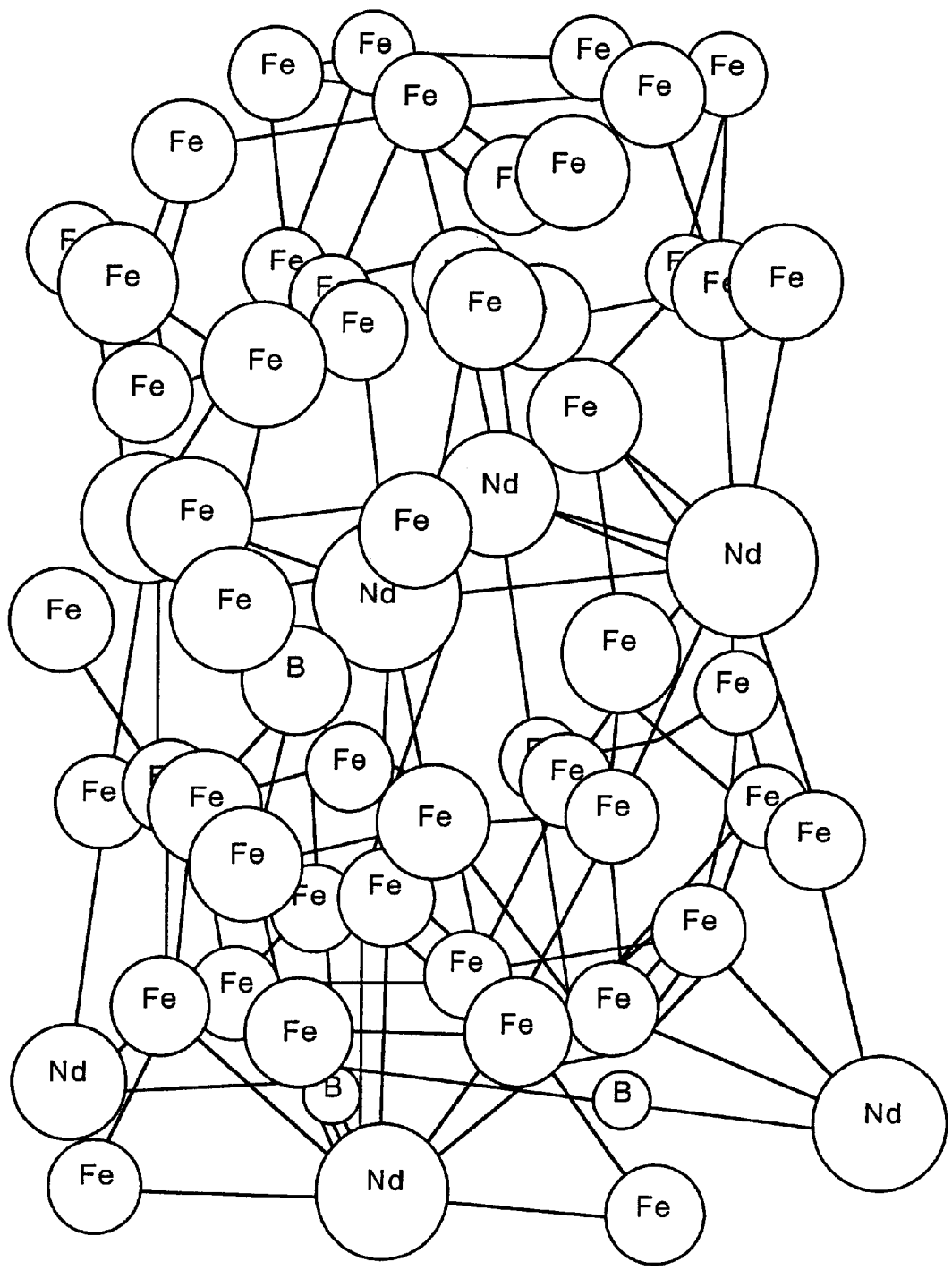
FIG. 1 is a diagram which shows a unit cell structure in an $Nd_2Fe_{14}B$ crystal used in calculation when the magnetic interaction calculation method of the present invention is evaluated.

Embodiments of the magnetic interaction calculation method or the magnetic characteristic value calculation method according to the present invention will be described below with reference to the accompanying drawings. It should be noted that the present invention is not limited to this embodiment.

Molecular orbitals $\phi_i$ can be expressed as a linear combination of atomic orbitals $\chi_a$ by the following equation:

$$\phi_i = \sum_a c_{ai} \chi_a$$

Where reference symbol $c_{ai}$ denotes an expansion coefficient, and satisfies the following standardizing condition:

$$\sum_a \sum_b c_{ai}^T S_{ab} c_{bi} = 1 \quad (1)$$

where $S_{ab}$ is an overlap integral between $\chi_a$ and $\chi_b$.

Because the molecular orbitals $\phi_i$ are canonical orbitals to establish a standard orthogonal system (perfect system), localized magnetic orbitals $\eta_a$ can be developed as expressed in the following equation (2) by using $\phi_i$ as a base:

$$\eta_a = \sum_i T_{ai} \phi_i \quad (2)$$

It is assumed that, as a sum in the equation (2), $\phi_i$ is taken about occupied orbitals when the localized magnetic orbitals $\eta_a$ are occupied orbitals ($\eta_a^{occ}$), and $\phi_i$ is taken about unoccupied orbitals when the localized magnetic orbitals $\eta_a$ is unoccupied orbitals $\eta_a^{vac}$.

A reference orbital $\omega_a$ which is localized on the atomic orbitals $\chi_a$ is defined by using an inverse matrix $c_{ai}^{-1}$ of the expansion coefficient $c_{ai}$ as follows:

$$\omega_a = \sum_i c_{ai}^{-1} \phi_i$$

In this equation, the reference orbitals $\omega_a$ are an asymptotic solution. The inverse matrix $c_{ai}^{-1}$ can be calculated from the equation (1).

The localized magnetic orbitals $\eta_a$ can be obtained from the reference orbitals $\omega_a$ and the next maximum overlap condition:

$$\sum_a |\langle \eta_a | \omega_a \rangle| = \text{maximum} \quad (3)$$

In addition, the equation (3) is resolved to a maximum problem of $\Omega(T)$ expressed by the following equation (4):

$$\Omega(T) = \sum_a |\langle \eta_a | \omega_a \rangle|^2 \quad (4)$$

$$= \sum_a \left| \sum_i T_{ai} * \langle \phi_i | \omega_a \rangle \right|^2$$

$$= \sum_a \left| \sum_i \sum_j T_{ai} * c_{aj}^{-1} \langle \phi_i | \phi_j \rangle \right|^2$$

$$= \sum_a \left| \sum_i T_{ai} * c_{ai}^{-1} \right|^2$$

As is apparent from the equation (4), the localized magnetic orbitals $\eta_a$ can be expressed as a subspace of the inverse matrix $c_{ai}^{-1}$. Therefore, when a subspace matrix of the inverse matrix $c_{ai}^{-1}$ defined by the equation (4) is represented by $d_{ia}$, according to the equation (2), the localized magnetic orbitals $\eta_a$ can be expressed with respect to occupied orbitals $\eta_a^{occ}$ and unoccupied orbitals $\eta_a^{vac}$ given by the following equations:

$$\eta_a^{occ} = \left( \sum_i^{occ} d_{ia}^2 \right)^{1/2} \sum_i^{occ} d_{ia} \phi_i$$

$$\eta_a^{vac} = \left( \sum_i^{vac} d_{ia}^2 \right)^{-1/2} \sum_i^{vac} d_{ia} \phi_i$$

The occupied orbitals $\eta_a^{occ}$ and the unoccupied orbitals $\eta_a^{vac}$ have one-to-one correspondence (isomorphism mapping) with respect to the reference orbitals $\omega_a$ localized in the atomic orbitals $\chi_a$.

An electron count $L_a^{occ}$ and a hole count $L_a^{vac}$ held by the occupied orbitals $\eta_a^{occ}$ and the unoccupied orbitals $\eta_a^{vac}$ are given by the following equations, respectively:

$$L_a^{occ} = \sum_i^{occ} d_{ia}^2$$

$$L_a^{vac} = \sum_i^{vac} d_{ia}^2$$

When the orbital energies of the occupied orbitals $\eta_a^{occ}$ and the unoccupied orbitals $\eta_a^{vac}$ are represented by $\lambda_a^{occ}$ and $\lambda_a^{vac}$, respectively, the orbital energies $\lambda_a^{occ}$ and $\lambda_a^{vac}$ are given by the following equations:

$$\lambda_a^{occ} = \left( \sum_i^{occ} d_{ia}^2 \right)^{-1/2} \sum_i^{occ} d_{ia} \varepsilon_i$$

$$\lambda_a^{vac} = \left( \sum_i^{vac} d_{ia}^2 \right)^{-1/2} \sum_i^{vac} d_{ia} \varepsilon_i$$

where $å_i$ is an orbital energy of the molecular orbitals $\phi_i$.

According to the above equations, an ionization potential $IP_a$ and an electron affinity $EA_a$ in the localized magnetic orbitals can be expressed from the orbital energy $\lambda_a^{occ}$ and the orbital energy $\lambda_a^{vac}$ as follows:

$$IP_a = -\lambda_a^{occ}$$

$$EA_a = -\lambda_a^{vac}$$

In the above description, the molecular models are explained. However, since the present invention can be similarly extended to corresponding crystal orbitals in a crystalline compound or a high polymer compound, a description thereof will be omitted.

A magnetic interaction based on localized magnetic orbitals will be described below. An effective exchange interaction $J_{ab}^{eff}$ representing a magnetic interaction is approximated by the sum of a direct exchange interaction $J_{ab}^{EX}$ and a super exchange interaction $J_{ab}^{SE}$.

$$J_{ab}^{eff} = J_{ab}^{EX} + J_{ab}^{SE}$$

The direct (potential) exchange interaction $J_{ab}^{EX}$ based on the localized magnetic orbitals is expressed by the following equation:

$$J_{ab}^{EX} = 2K_{ab}L_a^{occ}L_b^{occ}$$

In this equation, an exchange integral $K_{ab}$ is given by the following equation:

$$K_{ab} = \int\int \eta_a^*(1)\eta_b^*(2)\frac{1}{r_{12}}\eta_a(2)\eta_b(1)d\tau_1 d\tau_2$$

and $L_a^{occ}$ and $L_b^{occ}$ denote the numbers of electrons of the occupied orbitals $\eta_a^{occ}$ and $\eta_b^{occ}$ in the localized magnetic orbitals.

A super exchange interaction $J_{ab}^{SE}$ based on the localized magnetic orbitals is expressed by the following equation:

$$J_{ab}^{SE} = K_{ab}^{SE} L_a^{occ} L_b^{vac}$$

In this equation, by using a transfer integral $t_{ab}$ and an overlap integral $s_{ab}$, a kinematic integral $K_{ab}^{SE}$ is given by the following equation:

$$K_{ab}^{SE} = 2t_{ab}s_{ab}$$

According to the above description, a model which calculates a magnetic interaction can be achieved. Therefore, a magnetic characteristic value is then calculated by using the model, and is compared with an experimental value to be verified. Here, as the magnetic characteristic value, a Curie temperature or a residual magnetic flux density are evaluated.

In a first embodiment, in order to examine the reliability and versatility of the present invention, the physicality value of a neodymium-based rare earth magnet was evaluated. The neodymium-based rare earth magnet is an intermediate electron system having itinerant electrons and localized electrons. A unit cell in the crystal of the electron system consists of 68 atoms. This electron system is a huge system which cannot be easily calculated by a conventional band calculation method.

FIG. 1 is a diagram which shows a unit cell structure in an $Nd_2Fe_{14}B$ crystal used in calculation. Here, the theoretical value of a Curie temperature obtained when Fe is displaced with Co is compared with a calculated value based on the present invention. The Curie temperature is a target to be evaluated because the Curie temperature is an important measure with which an effective exchange interaction energy obtained from localized magnetic crystal orbitals is compared with the experimental value. Since Fe can be completely replaced with Co, the calculation result and the experiment result can be effectively compared with each other by a replacement ratio (dopant ratio) of Co. The effect of the dopant of Co is considered by using imaginary crystal approximation which is a kind of mean field approximation.

Figure 2:
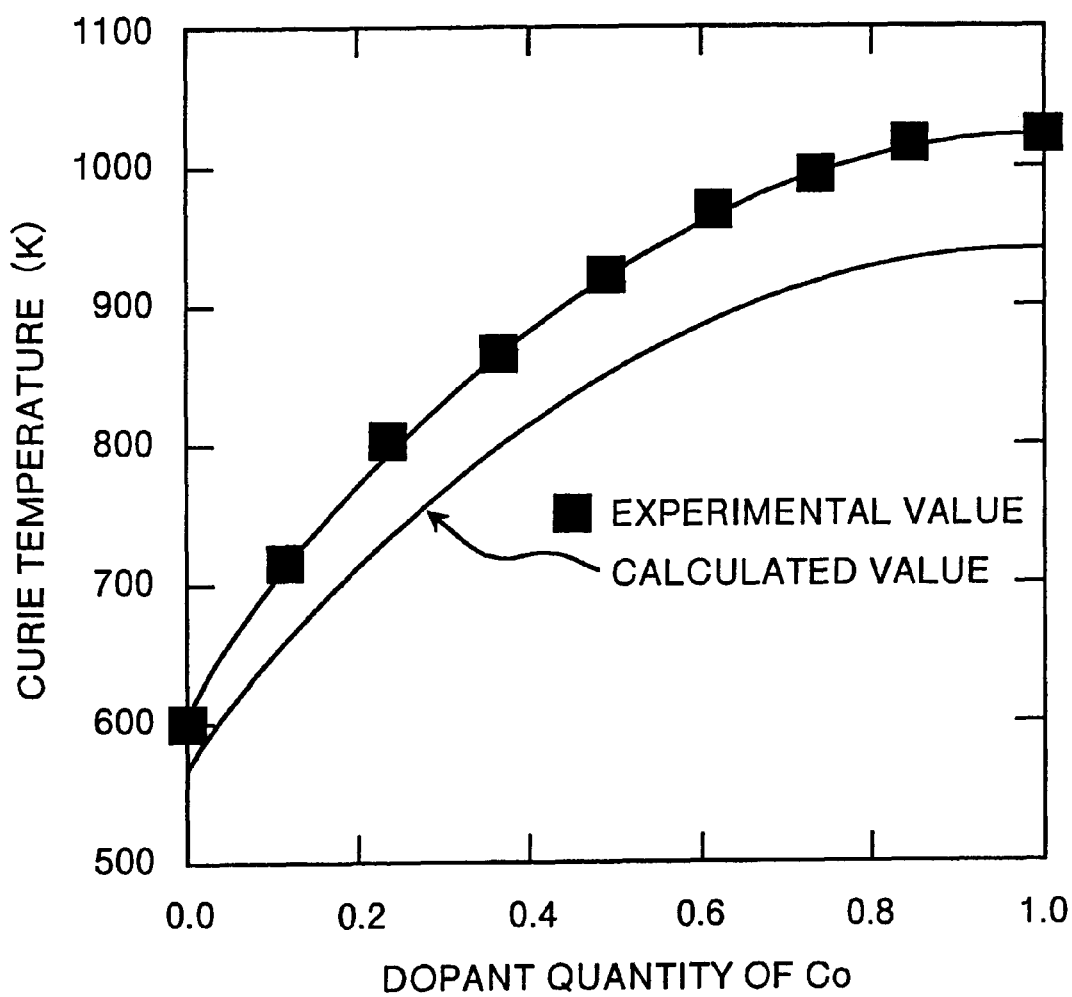
FIG. 2 is a comparative graph which shows Co-dopant quantity dependence of Curie temperature in $Nd_2(Fe_{1-x}Co_x)_{14}B$.

More specifically, the Curie temperature in an $Nd_2(Fe_{1-x}Co_x)_{14}B$ crystal was evaluated. FIG. 2 is a comparative graph which shows Co-dopant quantity dependence of the Curie temperature in $Nd_2(Fe_{1-x}Co_x)_{14}B$. The experiment result provided here is quoted from a reference "Y. Matsuura et al. Appl. Phys. Lett., 46, 308 (1985)". As is apparent from FIG. 2, the Curie temperature with respect to the Co-dopant quantity exhibits the same trend in the experiment and the calculation.

In particular, in an area in which the Co-dopant quantity is 25% or less, the experimental value and the calculated value of the Curie temperature are almost equal to each other. Therefore, it was confirmed that the Curie temperature calculated from the present invention could be "quantitatively" compared with the experiment result. More specifically, it was confirmed that an effective exchange interaction energy based on the present invention was reliable.

Figure 3:
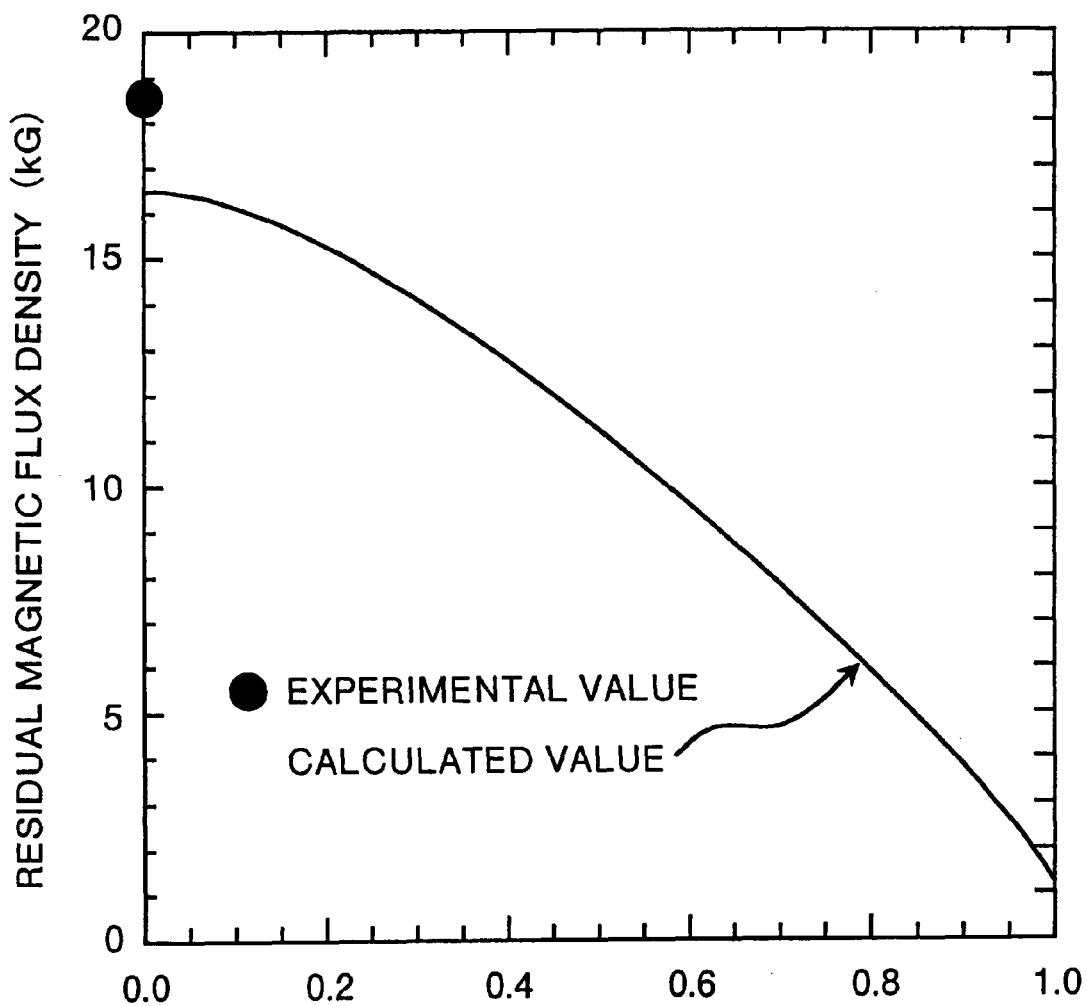
FIG. 3 is a comparative graph which shows Co-dopant quantity dependence of a residual magnetic flux density in $Nd_2(Fe_{1-x}Co_x)_{14}B$.

Since it was understood by the present invention that the Curie temperature was quantitatively approximate to an actually measured value, simulation for Co-dopant dependence of a residual magnetic flux density was performed in a similar system. FIG. 3 is a comparative graph which shows Co-dopant dependence of a residual magnetic flux density in $Nd_2(Fe_{1-x}Co_x)_{14}B$. The experiment result provided here was measured at 4.2 K, and is quoted from a reference "S. Hirosawa et al. J. Appl. Phys., 59,873 (1986)". Only the experiment result related to $Nd_2Fe_{14}B$ is described because the residual magnetic flux density of the $Nd_2(Fe_{1-x}Co_x)_{14}B$ crystal is not reported.

As shown in FIG. 3, the experimental value and the calculated value of a residual magnetic flux density in $Nd_2Fe_{14}B$ were 18.50 kG and 16.60 kG, respectively. It was confirmed that these values were almost equal to each other. As shown in FIG. 3, the residual magnetic flux density decreases as the Co-dopant quantity increases. This downward trend is the same as that of a result related to a saturated magnetic flux density. Therefore, a calculated value (physicality value) taken along the experimental value can be extremely effectively obtained based on the method of calculating a magnetic interaction according to the present invention.

Although the calculation based on the present invention was performed by an engineering workstation, the computation time was 50 minutes. Since it was estimated that the band calculation method based on the conventional density functional theory required at least a computation time of about several weeks, it was confirmed that magnetic characteristics could be easily calculated by the calculation method according to the present invention.

Figure 4:
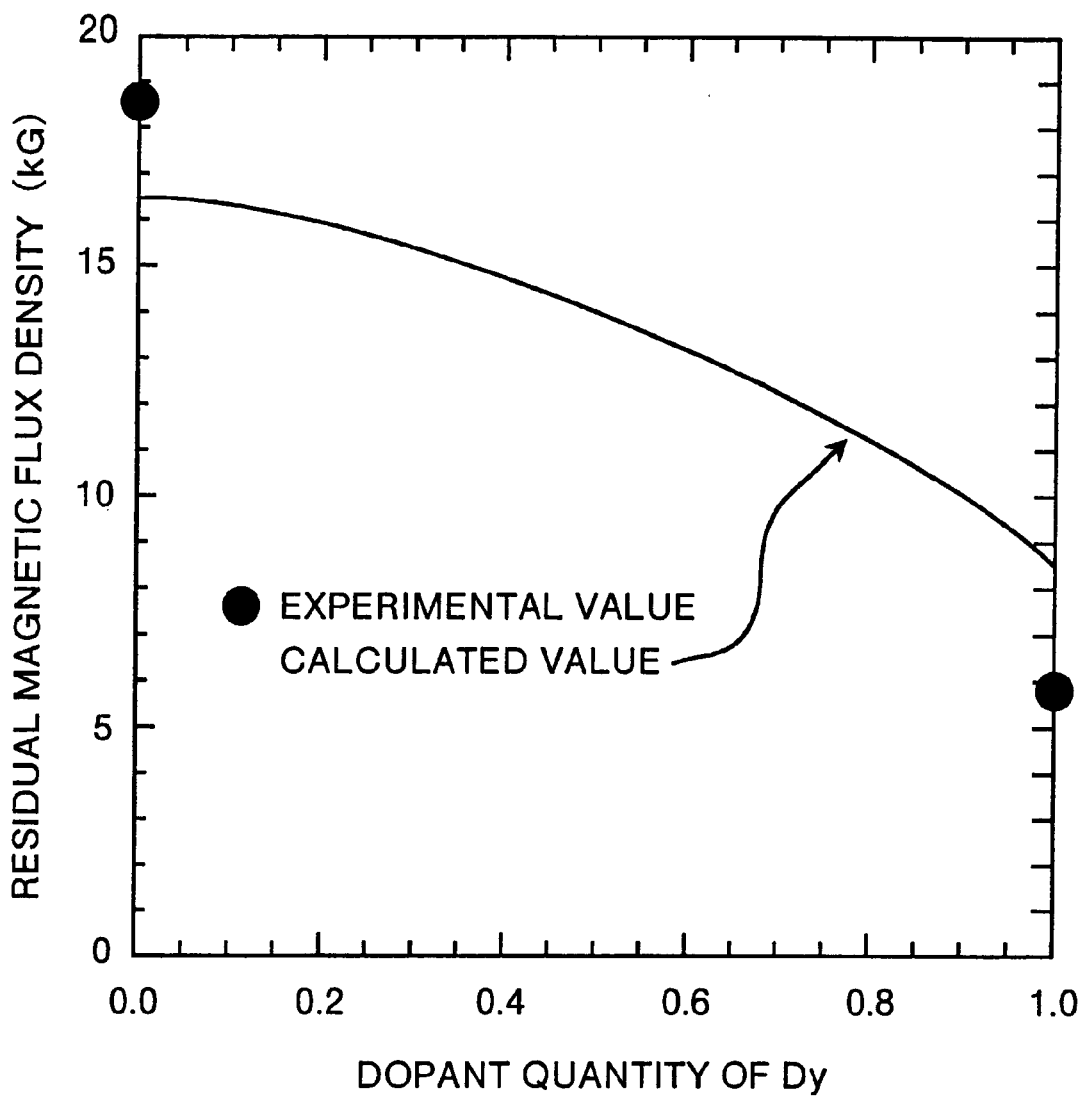
FIG. 4 is a comparative graph which shows Dy-dopant quantity dependence of residual magnetic flux density in an $(Nd_{1-x}Dy_x)_2Fe_{14}B$ crystal.

In a second embodiment, as in the first embodiment, comparative evaluation of a residual magnetic flux density of a $Dy_2Fe_{14}B$ crystal was performed. In addition, a calculation was also performed to an $(Nd_{1-x}Dy_x)_2Fe_{14}B$ crystal. FIG. 4 is a comparative graph which shows a Dy-dopant dependence of the residual magnetic flux density in the $(Nd_{1-x}Dy_x)_2Fe_{14}B$ crystal. The experiment result provided here is quoted from the reference "S. Hirosawa et al. J. Appl. Phys., 59,873 (1986)".

As shown in FIG. 4, the experimental value and the calculated value of a residual magnetic flux density in $Dy_2Fe_{14}B$ were 5.73 kG and 8.48 kG, respectively. When this calculated value is compared with the calculated value in $Nd_2Fe_{14}B$, it is understood that the calculated value can be quantitatively compared with the experimental value. The computation time required for this calculation was 55 minutes. Since it was estimated that the band calculation method based on the conventional density functional theory required at least a computation time of about several weeks, it was confirmed that magnetic characteristics could be easily calculated by the calculation method according to the present invention.

The embodiments according to the present invention have been described above. The concrete example of configuration is not limited to the embodiments, and the design of the configuration may be changed without departing from the spirit and scope of the invention.

For example, a computer executable program which causes a computer to execute the magnetic interaction calculation method or the magnetic value calculation method, and this program is recorded on a computer readable recording medium. The program recorded on the recording medium is loaded on the computer to be executed, so that the respective functions may be realized.

As described above, according to the present invention, the magnetic interaction in not only the itinerant electron system but also the localized electron system or the intermediate electron system across both the electron systems can be advantageously calculated by using the localized magnetic orbitals or the localized magnetic crystal orbitals. Therefore, the magnetic characteristic value in the localized electron system or the intermediate electron system across the both electron systems can be advantageously calculated. Furthermore, the magnetic characteristic values of large molecules, a crystalline compound, and a high polymer compound can be easily calculated and predicted advantageously.

Although the invention has been described with respect to a specific embodiment for a complete and clear disclosure, the appended claims are not to be thus limited but are to be construed as embodying all modifications and alternative constructions that may occur to one skilled in the art which fairly fall within the basic teaching herein set forth.

What is claimed is:

1. A magnetic interaction calculation method comprising:
   calculating a magnetic interaction of molecules using a localized magnetic orbital $\eta_a$ which satisfies a maximum overlap condition $$\sum_a |\langle \eta_a | \omega_a \rangle| = \text{maximum},$$

wherein $$\eta_a = \sum_i T_{ai} \phi_i$$

and $\omega_a$ is a reference orbital given by $$\omega_a = \sum_i c_{ai}^{-1} \phi_i \text{ where } \phi_i = \sum_a c_{ai} \chi_a$$

is a molecular orbital expressed as a linear combination of an atomic orbital $\chi_a$, $c_{ai}$ is an expansion coefficient, $c_{ai}^{-1}$ is an inverse matrix of the expansion coefficient $c_{ai}$, and $T_{ai}$ is an expansion coefficient of the a-th orbital $\eta_a$ for the i-th molecular orbital $\phi_i$.

2. The method according to claim 1, including using, as the magnetic interaction, an orthogonal exchange interaction $2K_{ab}L_a^{occ}L_b^{occ}$ obtained using a potential exchange integral $K_{ab}$ in localized magnetic orbitals $\eta_a$ and $\eta_b$, and electron counts $L_a^{occ}$ and $L_b^{occ}$ of occupied orbitals.

3. The method according to claim 1, using, as the magnetic interaction, a super exchange interaction $K^{SE}_{ab}L_a^{occ}L_b^{vac}$ obtained using a kinematic exchange integral $K^{SE}_{ab}$ in localized magnetic orbitals $\eta_a$ and $\eta_b$, an electron count $L_a^{occ}$ of occupied orbitals, and a hole count $L_b^{vac}$ of unoccupied orbitals.

4. A magnetic interaction calculation method comprising:
   calculating a magnetic interaction of crystalline compounds or high polymer compounds using a localized magnetic crystal orbital $\eta_a(k)$ which satisfies a maximum overlap condition $$\sum_a |\langle \eta_a | \omega_a \rangle| = \text{maximum},$$

wherein $\eta_a(k) = \sum_i T_{ai}(k)\phi_i(k)$ and $\omega_a(k)$ is a reference orbital given by $$\omega_a(k) = \sum_i c_{ai}(k)^{-1} \phi_i(k) \text{ where}$$

$$\phi_i(k) = \sum_a c_{ai}(k) \sum_R \exp(ikR) \chi_a(R)$$

is a crystal orbital expressed as a linear combination of an atomic orbital $\chi_a$, $c_{ai}(k)$ is an expansion coefficient, $c_{ai}(k)^{-1}$ is an inverse matrix of the expansion coefficient $c_{ai}(k)$, $T_{ai}(k)$ is an expansion coefficient of the a-th localized magnetic orbital $\eta_a(k)$ for the i-th crystal orbital $\phi_i(k)$, k is a wave vector ranging from $-\pi/c$ to $\pi/c$, where c is a primitive vector, and R is a vector representing crystal periods.

5. The method according to claim 4, including using, as the magnetic interaction, an orthogonal exchange interaction $2K_{ab}L_a^{occ}L_b^{occ}$ obtained using a potential exchange integral $K_{ab}$ in localized magnetic crystal orbitals $\eta_a(k)$ and $\eta_b(k)$ and electron counts $L_a^{occ}$ and $L_b^{occ}$ of occupied orbitals, is employed.

6. The method according to claim 4, including using, as the magnetic interaction, a super exchange interaction $K^{SE}_{ab}L_a^{occ}L_b^{vac}$ obtained using a kinematic exchange integral $K^{SE}_{ab}$ in localized magnetic crystal orbitals $\eta_a(k)$ and $\eta_b(k)$, an electron count $L_a^{occ}$ of occupied orbitals, and a hole count $L_b^{vac}$ of unoccupied orbitals.

* * * * *